(12) United States Patent
Eidamshaus et al.

(10) Patent No.: US 11,274,072 B2
(45) Date of Patent: Mar. 15, 2022

(54) PROCESS FOR THE CONTINUOUS PREPARATION OF 1,2-PROPYLENE DIAMINE (1,2-PDA) AND DIMETHYLDIETHYLENE TRIAMINE (DMDETA)

(71) Applicant: BASF SE, Ludwigshafen am Rhein (DE)

(72) Inventors: Christian Eidamshaus, Ludwigshafen am Rhein (DE); Johann-Peter Melder, Ludwigshafen am Rhein (DE); Joerg Pastre, Ludwigshafen am Rhein (DE); Hans-Juergen Pallasch, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 94 days.

(21) Appl. No.: 16/768,505

(22) PCT Filed: Nov. 19, 2018

(86) PCT No.: PCT/EP2018/081728
§ 371 (c)(1),
(2) Date: May 29, 2020

(87) PCT Pub. No.: WO2019/105782
PCT Pub. Date: Jun. 6, 2019

(65) Prior Publication Data
US 2020/0385332 A1    Dec. 10, 2020

(30) Foreign Application Priority Data

Nov. 30, 2017 (EP) ..................................... 17204658

(51) Int. Cl.
*C07C 209/16* (2006.01)
*B01D 3/14* (2006.01)
(Continued)

(52) U.S. Cl.
CPC ............ *C07C 209/16* (2013.01); *B01D 3/143* (2013.01); *B01J 21/04* (2013.01); *B01J 23/72* (2013.01);
(Continued)

(58) Field of Classification Search
None
See application file for complete search history.

(56) References Cited

U.S. PATENT DOCUMENTS

2011/0151615 A1    6/2011   Gordon et al.

FOREIGN PATENT DOCUMENTS

| CN | 103819344 A | 5/2014 |
| CN | 104693037 A | 6/2015 |

(Continued)

OTHER PUBLICATIONS

International Preliminary Report on Patentability received for PCT Patent Application No. PCT/EP2018/081728, dated Nov. 22, 2019, 17 pages (5 pages of English Translation and 12 pages of Original Document).

(Continued)

*Primary Examiner* — Sudhakar Katakam
*Assistant Examiner* — Jennifer C Sawyer
(74) *Attorney, Agent, or Firm* — Faegre Drinker Biddle & Reath LLP

(57) ABSTRACT

A process for the continuous preparation of 1,2-propylenediamine (1,2-PDA) and dimethyldiethylenetriamine (DMDETA) via reaction of monoisopropanolamine (MIPOA) with ammonia in the presence of hydrogen and a supported heterogeneous hydrogenation catalyst (catalyst), wherein the reaction is effected in the liquid phase at an absolute pressure in the range from 60 to 170 bar.

16 Claims, 1 Drawing Sheet

(51) Int. Cl.
*B01J 21/04* (2006.01)
*B01J 23/72* (2006.01)
*B01J 23/75* (2006.01)
*B01J 23/755* (2006.01)
*C07C 209/02* (2006.01)
*C07C 209/84* (2006.01)
*C07C 211/11* (2006.01)
*C07C 211/14* (2006.01)

(52) U.S. Cl.
CPC ............ *B01J 23/75* (2013.01); *B01J 23/755* (2013.01); *C07C 209/02* (2013.01); *C07C 209/84* (2013.01); *C07C 211/11* (2013.01); *C07C 211/14* (2013.01)

(56) References Cited

FOREIGN PATENT DOCUMENTS

| | | |
|---|---|---|
| WO | 03/51508 A1 | 6/2003 |
| WO | 2008/006750 A1 | 1/2008 |
| WO | 2009/080506 A1 | 7/2009 |
| WO | 2009/080507 A1 | 7/2009 |
| WO | 2009/080508 A1 | 7/2009 |
| WO | 2009/114438 A2 | 9/2009 |
| WO | 2011/067199 A1 | 6/2011 |
| WO | 2013/072289 A1 | 5/2013 |

OTHER PUBLICATIONS

International Search Report and Written Opinion received for PCT Patent Application No. PCT/EP2018/081728, dated Feb. 22, 2019, 11 pages (2 pages of English Translation and 9 pages of Original Document).

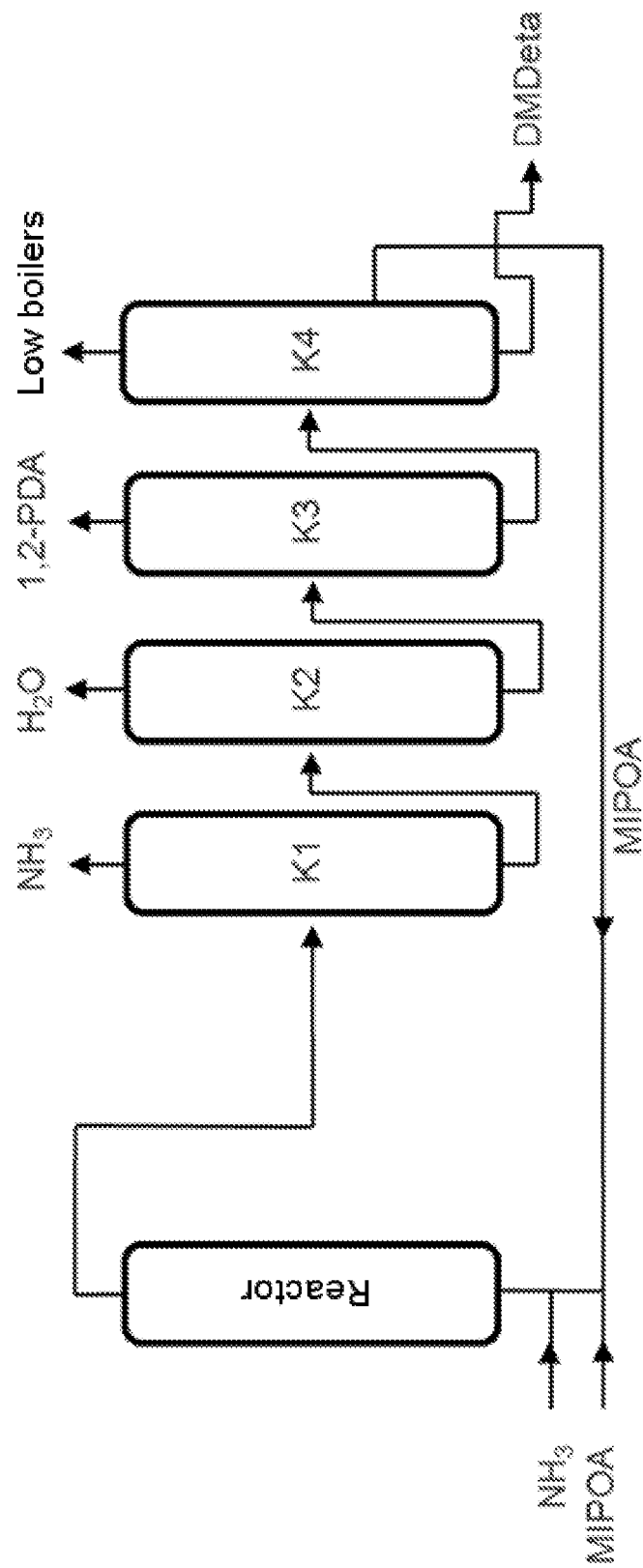

PROCESS FOR THE CONTINUOUS PREPARATION OF 1,2-PROPYLENE DIAMINE (1,2-PDA) AND DIMETHYLDIETHYLENE TRIAMINE (DMDETA)

CROSS-REFERENCE TO RELATED APPLICATIONS

This application is a national stage application (under 35 U.S.C. § 371) of PCT/EP2018/081728, filed Nov. 19, 2018, which claims benefit of European Application No. 17204658.3, filed Nov. 30, 2017, both of which are incorporated herein by reference in their entirety.

The application relates to a process for the continuous preparation of 1,2-propylenediamine (1,2-PDA) and dimethyldiethylenetriamine (DMDETA) via reaction of monoisopropanolamine (MIPOA) with ammonia in the presence of hydrogen and a supported heterogeneous hydrogenation catalyst (catalyst).

STATE OF THE ART 1,2-PDA is used inter alia as an intermediate in the production of fuel additives, surfactants, medicaments and crop protection products, curing agents for epoxy resins, catalysts for polyurethanes, intermediates for the preparation of quaternary ammonium compounds, plasticizers, corrosion inhibitors, synthetic resins, ion exchangers, textile auxiliaries, dyes, vulcanization accelerators and/or emulsifiers. For example, DMDETA can be used as an epoxy curing agent.

WO 03/051508 A1 (Huntsman Petrochemical Corp.) relates to processes for aminating alcohols using specific Cu/Ni/Zr/Sn-containing catalysts which in a further embodiment comprise Cr instead of Zr (see page 4, lines 10-16). The catalysts described in this WO application do not comprise any aluminum oxide or cobalt.

WO 2008/006750 A1 (BASF AG) relates to particular Pb, Bi, Sn, Sb and/or In-doped, zirconium dioxide-, copper-, nickel- and cobalt-containing catalysts and to the use thereof in processes for preparing an amine by reacting a primary or secondary alcohol, aldehyde and/or ketone with hydrogen and ammonia or a primary or secondary amine. Aluminum oxide supports are not taught.

WO 2009/080507 A1 (BASF SE) relates to particular Sn- and Co-doped, zirconium dioxide-, copper- and nickel-containing catalysts and to the use thereof in processes for preparing an amine by reacting a primary or secondary alcohol, aldehyde and/or ketone with hydrogen and ammonia or a primary or second amine. Aluminum oxide supports are not taught.

WO 2009/080506 A1 (BASF SE) describes particular Pb, Bi, Sn, Mo, Sb and/or P-doped, zirconium dioxide-, nickel- and iron-containing catalysts and the use thereof in processes for preparing an amine by reacting a primary or secondary alcohol, aldehyde and/or ketone with hydrogen and ammonia or a primary or secondary amine. Aluminum oxide supports are not taught. The catalysts preferably do not comprise any Cu or Co.

WO 2009/080508 A1 (BASF SE) teaches particular Pb, Bi, Sn and/or Sb-doped, zirconium dioxide-, copper-, nickel-, cobalt- and iron-containing catalysts and the use thereof in processes for preparing an amine by reacting a primary or secondary alcohol, aldehyde and/or ketone with hydrogen and ammonia or a primary or secondary amine. Aluminum oxide supports are not taught.

WO 2009/114438 A2 (Huntsman Petrochem. Corp.) relates to the amination of cyclohexanedimethanol in the presence of hydrogen and $ZrO_2$-supported metal catalysts, e.g. $ZrO_2$/Cu/Ni/Sn.

1,2-PDA can be prepared by reacting monoisopropanolamine (MIPOA) with ammonia and hydrogen in the presence of a suitable catalyst.

WO 2011/067199 A1 (BASF SE) describes a process for preparing an amine by reacting a primary or secondary alcohol, aldehyde or ketone with hydrogen and ammonia in the presence of a supported copper-, nickel- and cobalt-containing catalyst which comprises in the range from 0.2% to 5.0% by weight of oxygen-containing compounds of tin, calculated as SnO. The description describes the reaction of 2-hydroxypropylamine and $NH_3$ (page 25, line 25) in general.

CN 104693037 A (Dalian Institute of Chemical Physics) describes the reaction of isopropanolamine and ammonia in the presence of hydrogen at a pressure of 20 to 250 bar and a temperature of 120 to 230° C. over a supported catalyst comprising Ni and/or Cu and also promoters selected from the group of Fe, Cu, Ru, Re, K, Zn and B, with the support used being $SiO_2$ and/or $Al_2O_3$.

DMDETA can for example be prepared by reacting 1,2-PDA and methylaziridine in a yield of up to 24%—described in US 2011/151615 A1 (President and Fellows of Harvard College). It is also possible to react 1,2-dichloropropane with ammonia (K. V. Chernitskii, V. A. Bobylev, J. Gen. Chem. USSR, 1990, 60, 1636-1643). Furthermore, it is theoretically possible that DMDETA is obtained as what is called a coproduct (product of value) when preparing 1,2-PDA. This involves 1,2-PDA already formed reacting with unconverted MIPOA to give DMDETA with the elimination of water. However, it is often not possible to obtain DMDETA in sufficient amounts since it cyclizes to give dimethylpiperazine with the elimination of ammonia. The formation of the product of value DMDETA has therefore not been described in the prior art.

The present invention was based on the object of remedying one or more disadvantages of the prior art. In particular, the intention was to find a process for preparing 1,2-PDA in which DMDETA is formed in significant amounts at the same time. Conditions should be found that can be established technically simply and therefore cost-effectively and which make it possible to conduct the process efficiently, in particular with a high conversion, high yield, space-time yield (STY) and selectivity with a simultaneously high mechanical stability of the catalyst shaped body. In addition, ways should be found to obtain 1,2-PDA and DMDETA with as high a purity as possible.

> [Space-time yields are reported in 'product quantity/
> (catalyst volume·time)'(kg/($I_{cat.}$·h))
> and/or 'product quantity/(reactor volume·time)'
> (kg/($I_{reactor}$·h))].

Surprisingly, a process was found for the continuous preparation of 1,2-propylenediamine (1,2-PDA) and dimethyldiethylenetriamine (DMDETA) via reaction of monoisopropanolamine (MIPOA) with ammonia in the presence of hydrogen and a supported heterogeneous hydrogenation catalyst (catalyst), wherein the reaction is effected in the liquid phase at an absolute pressure in the range from 60 to 170 bar.

DESCRIPTION OF THE INVENTION

For example, catalysts can be used, the catalytically active composition of which, prior to the reduction thereof with hydrogen, comprises oxygen-containing compounds of aluminum and oxygen-containing compounds of copper, of nickel and/or of cobalt.

Preference is given to catalysts, the catalytically active composition of which, prior to the reduction thereof with hydrogen, comprises oxygen-containing compounds of aluminum, of copper, of nickel and of cobalt and in the range from 0.2% to 5.0% by weight of oxygen-containing compounds of tin, calculated as SnO.

Catalysts, the catalytically active composition of which, prior to the reduction thereof with hydrogen, comprises in the range from 15% to 80% by weight of oxygen-containing compounds of aluminum, calculated as $Al_2O_3$,
1% to 20% by weight of oxygen-containing compounds of copper, calculated as CuO,
5% to 35% by weight of oxygen-containing compounds of nickel, calculated as NiO,
5% to 35% by weight of oxygen-containing compounds of cobalt, calculated as CoO, and
0.2% to 5.0% by weight of oxygen-containing compounds of tin, calculated as SnO,
are in particular used in the abovementioned amination process.

Preferred reactors are tubular reactors. Examples of suitable reactors comprising a cycle gas stream may be found in Ullmann's Encyclopedia of Industrial Chemistry, 5th ed., vol. B 4, pages 199-238, "Fixed-Bed Reactors".

Alternatively, the reaction is advantageously effected in a shell and tube reactor or in a single-stream plant. In a single-stream plant, the tubular reactor in which the reaction takes place may be composed of a series connection of a plurality (e.g., two or three) of individual tubular reactors. A possible and advantageous option here is the intermediate introduction of feed (comprising the MIPOA and/or ammonia and/or $H_2$) and/or cycle gas and/or reactor output from a downstream reactor.

The amount of cycle gas, in the case of an $H_2$ content of 80% by volume, is preferably in the range from 10 to 450 $Nm^3/[m^3$ of catalyst (bed volume)·h], in particular in the range from 15 to 450 $Nm^3/[m^3$ of catalyst (bed volume)·h], more particularly in the range from 20 to 400 $Nm^3/[m^3$ of catalyst (bed volume)·h], very particularly in the range from 25 to 400 $Nm^3/[m^3$ of catalyst (bed volume)·h], for example 35 to 360 $Nm^3/[m^3$ of catalyst (bed volume)·h].

For a different $H_2$ content, the abovementioned cycle gas amounts accordingly change mathematically in order to keep the $H_2$ amount (in $Nm^3/[m^3$ of catalyst (bed volume)·h]) constant.

[$Nm^3$=standard cubic meter=volume converted to standard conditions (20° C., 1 bar abs.)]. (Standard pressure=1 bar abs.)

In the process according to the invention, the catalysts are preferably used in the form of catalysts consisting only of catalytically active composition and optionally a shaping aid (such as graphite or stearic acid, for example) if the catalyst is used in the form of shaped bodies, that is to say do not comprise any other catalytically active accompanying substances.

In this context, the oxidic support material aluminum oxide ($Al_2O_3$) is considered to belong to the catalytically active composition.

The catalysts are used in such a way that the catalytically active composition, ground to a powder, is introduced into the reaction vessel or that the catalytically active composition, following grinding, mixing with shaping aids, shaping, and heat treatment, is arranged in the reactor in the form of shaped catalyst bodies—for example as tablets, beads, rings, extrudates (e.g. strands).

The concentration figures (in % by weight) of the components of the catalyst are in each case based—unless otherwise indicated—on the catalytically active composition of the finished catalyst after the final heat treatment thereof and prior to the reduction thereof with hydrogen.

The catalytically active composition of the catalyst, after the final heat treatment thereof and prior to the reduction thereof with hydrogen, is defined as the sum of the masses of the catalytically active constituents and of the aforementioned catalyst support materials and comprises substantially the following constituents:

aluminum oxide ($Al_2O_3$), oxygen-containing compounds of copper, of nickel, and of cobalt and oxygen-containing compounds of tin.

The sum of the aforementioned constituents of the catalytically active composition is typically 70% to 100% by weight, preferably 80% to 100% by weight, particularly preferably 90% to 100% by weight, particularly >95% by weight, very particularly >98% by weight, especially >99% by weight, for example, with particular preference, 100% by weight.

The catalytically active composition of the catalysts according to the invention and of those used in the process according to the invention may further comprise one or more elements (oxidation state 0) or inorganic or organic compounds thereof, selected from groups IA to VI A and I B to VII B and VIII of the Periodic Table.

Examples of such elements and compounds thereof are as follows:

transition metals, such as Mn or $MnO_2$, W or tungsten oxides, Ta or tantalum oxides, Nb or niobium oxides or niobium oxalate, V or vanadium oxides or vanadyl pyrophosphate;

lanthanides, such as Ce or $CeO_2$ or Pr or $Pr_2O_3$; alkaline earth metal oxides, such as SrO;

alkaline earth metal carbonates, such as $MgCO_3$, $CaCO_3$, and $BaCO_3$; and boron oxide ($B_2O_3$).

The catalytically active composition of the catalysts according to the invention and of those used in the process according to the invention preferably does not comprise any rhenium, any ruthenium, any iron and/or any zinc, in each case either in metallic form (oxidation state=0) or in an ionic form (oxidation state≠0), especially oxidized form.

The catalytically active composition of the catalysts according to the invention and of those used in the process according to the invention preferably does not comprise any silver and/or any molybdenum, in each case either in metallic form (oxidation state=0) or in an ionic form (oxidation state≠0), especially oxidized form.

In one particularly preferred embodiment, the catalytically active composition of the catalysts according to the invention and of those used in the process according to the invention does not comprise any further catalytically active component, either in elemental form (oxidation state=0) or in ionic form (oxidation state≠0).

In the particularly preferred embodiment, the catalytically active composition is not doped with further metals or metal compounds.

Preferably, however, this excludes typical accompanying trace elements originating from the extraction of Cu, Co, Ni and/or Sn metal.

The catalytically active composition of the catalyst preferably does not comprise any oxygen-containing compounds of silicon and/or of zirconium.

The catalytically active composition of the catalyst preferably does not comprise any oxygen-containing compounds of titanium and/or of chromium.

The catalytically active composition of the catalyst, prior to the reduction thereof with hydrogen, comprises in the range from 0.2% to 5.0% by weight, particularly in the range from 0.4% to 4.0% by weight, more particularly in the range from 0.6% to 3.0% by weight, more particularly preferably in the range from 0.7% to 2.5% by weight, of oxygen-containing compounds of tin, calculated as SnO.

The catalytically active composition of the catalyst, prior to the reduction thereof with hydrogen, comprises preferably in the range from 5.0% to 35% by weight, particularly in the range from 10% to 30% by weight, more particularly in the range from 12% to 28% by weight, very particularly 15% to 25% by weight, of oxygen-containing compounds of cobalt, calculated as CoO.

The catalytically active composition of the catalyst, prior to the reduction thereof with hydrogen, further preferably comprises in the range from
15% to 80% by weight, particularly 30% to 70% by weight, more particularly 35% to 65% by weight, of oxygen-containing compounds of aluminum, in each case calculated as $Al_2O_3$,
1% to 20% by weight, particularly 2% to 18% by weight, more particularly 5% to 15% by weight, of oxygen-containing compounds of copper, in each case calculated as CuO, and
5% to 35% by weight, particularly 10% to 30% by weight, more particularly 12% to 28% by weight, very particularly 15% to 25% by weight, of oxygen-containing compounds of nickel, in each case calculated as NiO.

The molar ratio of nickel to copper is preferably greater than 1, particularly preferably greater than 1.2, more particularly preferably in the range from 1.8 to 8.5.

The BET surface area (ISO 9277:1995) of the catalysts according to the invention and of those used in the process according to the invention is preferably in the range from 30 to 250 $m^2/g$, particularly in the range from 90 to 200 $m^2/g$, more particularly in the range from 130 to 190 $m^2/g$ (in each case prior to the reduction with hydrogen). These ranges are attained in particular by calcining temperatures during catalyst production in the range from 400 to 600° C., particularly 420 to 550° C. (cf. below).

A variety of processes are possible for producing the catalysts used in the process according to the invention. The catalysts are obtainable, for example, by peptizing pulverulent mixtures of the hydroxides, carbonates, oxides and/or other salts of the components with water, and subsequently extruding and heat-treating the resultant composition.

Precipitation methods are preferably used for producing the catalysts according to the invention. Accordingly, they can for example be obtained by coprecipitation of the nickel, cobalt, copper and Sn components from an aqueous salt solution comprising these elements by means of bases in the presence of a suspension of a sparingly soluble, oxygen-containing aluminum compound, and subsequent washing, drying, and calcining of the resultant precipitate. The sparingly soluble, oxygen-containing aluminum compounds that can be used include, for example, aluminum oxide, aluminum oxide hydrate, aluminum phosphates, aluminum borates and aluminum silicates. The suspensions of the sparingly soluble aluminum compounds may be prepared by suspending fine powders of these compounds in water with vigorous stirring. These suspensions are advantageously obtained by precipitating the sparingly soluble aluminum compounds from aqueous aluminum salt solutions by means of bases.

The catalysts according to the invention are preferably produced by coprecipitation (joint precipitation) of all of their components. For this purpose, an aqueous salt solution comprising the catalyst components is expediently admixed under hot conditions and with stirring with an aqueous base—for example sodium carbonate, sodium hydroxide, potassium carbonate, or potassium hydroxide—until precipitation is complete. It is also possible to work with alkali metal-free bases such as ammonia, ammonium carbonate, ammonium hydrogencarbonate, ammonium carbamate, ammonium oxalate, ammonium malonate, urotropine, urea, etc. The nature of the salts used is generally not critical: since the principal factor in this procedure is the water solubility of the salts, a criterion is their good water solubility required to prepare these comparatively highly concentrated salt solutions. It is considered to be self-evident that when selecting the salts of the individual components, the salts selected are of course only those having anions that do not lead to disruption, whether by causing undesired precipitation or by hindering or preventing precipitation by forming complexes.

The precipitates obtained in these precipitation reactions are generally chemically inhomogeneous and consist inter alia of mixtures of the oxides, oxide hydrates, hydroxides, carbonates, and insoluble and basic salts of the metals used. With regard to the filterability of the precipitates, it may prove to be favorable for them to be aged—that is to say for them to be left for a certain time after precipitation, optionally under hot conditions or with air being passed through.

The precipitates obtained after these precipitation processes are subjected to conventional further processing to give the catalysts according to the invention. The precipitates are first of all washed. The content of alkali metal which has been supplied by the (mineral) base which may have been used as a precipitant can be influenced via the duration of the washing operation and via the temperature and amount of the washing water Generally speaking, prolonging the washing time or increasing the temperature of the washing water will reduce the content of alkali metal. After the washing, the precipitated material is generally dried at 80 to 200° C., preferably at 100 to 150° C., and then calcined. The calcination is generally performed at temperatures between 300 and 800° C., preferably at 400 to 600° C., particularly at 420 to 550° C.

The catalysts according to the invention may also be produced via impregnation of aluminum oxide ($Al_2O_3$), which is present, for example, in the form of powder or shaped bodies, such as strands, tablets, beads, or rings.

The aluminum oxide is for example used in the amorphous, gamma, theta and/or delta form, as aluminum oxohydroxide (boehmite), preferably in the amorphous form.

Shaped bodies can be produced by the customary methods.

The impregnation is likewise effected by the customary methods, as described for example in A. B. Stiles, Catalyst Manufacture—Laboratory and Commercial Preparations, Marcel Dekker, New York (1983), by application of a respectively appropriate metal salt solution in one or more impregnation stages, with the metal salts used being, for example, corresponding nitrates, acetates, or chlorides. Following the impregnation, the composition is dried and optionally calcined.

Impregnation may be effected by what is called the "incipient wetness" method, in which the aluminum oxide is moistened, in accordance with its water uptake capacity, up to a maximum of saturation with the impregnation solution. Alternatively, impregnation can be effected in supernatant solution.

In the case of multistage impregnation processes, it is appropriate to dry and optionally to calcine between individual impregnation steps. Multistage impregnation can be advantageously employed especially when the aluminum oxide is to be loaded with a relatively large amount of metal.

For the application of the metal components to the aluminum oxide, impregnation can be effected simultaneously with all metal salts or successively in any desired sequence of the individual metal salts.

The catalysts produced by impregnation are subsequently dried and preferably also calcined, for example at the calcining temperature ranges already indicated above.

After calcination, the catalyst is appropriately conditioned, whether it be by adjusting it to a certain particle size by grinding, or by mixing it, after it has been ground, with shaping aids such as graphite or stearic acid, compressing it by means of a press into moldings, e.g. tablets, and subjecting it to heat treatment. The heat treatment temperatures preferably correspond here to the temperatures during the calcination.

The catalysts produced in this way comprise the catalytically active metals in the form of a mixture of their oxygen-containing compounds, that is to say in particular in the form of oxides and mixed oxides.

The catalysts produced for example as described above are stored as such and optionally traded. Prior to their use as catalysts, they are typically prereduced. They can, however, also be used without prereduction, in which case they are reduced under the conditions of hydrogenating amination by the hydrogen present in the reactor.

For the prereduction, the catalysts are first exposed to a nitrogen-hydrogen atmosphere at preferably 150 to 200° C. over a period of for example 12 to 20 hours and subsequently treated for up to approx. 24 hours more in a hydrogen atmosphere at preferably 200 to 400° C. In the course of this prereduction, some of the oxygen-containing metal compounds present in the catalysts are reduced to the corresponding metals, and as a result these are present together with the various kinds of oxygen compounds in the active form of the catalyst.

The process according to the invention is carried out continuously, with the catalyst preferably being arranged as a fixed bed in the reactor. It is possible for the flow toward the fixed catalyst bed to be either from the top or from the bottom.

The reactant used is MIPOA. There are two different constitutional isomers of MIPOA: 1-aminopropan-2-ol and 2-aminopropan-1-ol. Both isomers can be converted to 1,2-PDA according to the invention. Therefore, 1-aminopropan-2-ol, 2-aminopropan-1-ol or a mixture of these two isomers can be used. If such a mixture is used, a reference to MIPOA in this application always means both isomers. Preference is given to using MIPOA that has been prepared via reaction of propylene oxide with ammonia. This results predominantly in 1-aminopropan-2-ol, but also in small amounts of 2-aminopropan-1-ol, the proportion of which is typically 2% to 10% by weight, in particular 4% to 6% by weight, based on the total mass of the two isomers.

The DMDETA prepared according to the invention is obtained in three different constitutional isomers. These are N2-(2-aminopropyl)propane-1,2-diamine, N1-(2-aminopropyl)propane-1,2-diamine and N2-(2-amino-1-methylethyl)propane-1,2-diamine.

The ammonia is typically used in a 5-fold to 30-fold molar amount, preferably 6-fold to 29-fold molar amount, more preferably 7-fold to 28-fold molar amount, particularly 8-fold to 27-fold molar amount, especially in a 9-fold to 26-fold molar amount, in a 9-fold to 25-fold molar amount, a 9-fold to 20-fold molar amount or a 9-fold to 15-fold molar amount, in each case based on the MIPOA used.

The ammonia is preferably used without a further solvent (compressed gas, purity in particular 95% to 100% by weight).

The reactant MIPOA is preferably used in a purity of 95% to 100% by weight, particularly 98% to 100% by weight.

Preference is given to employing an offgas volume of 1 to 450 standard cubic meters/($m^3$ of catalyst (bed volume)·h), in particular 2 to 200 standard cubic meters/($m^3$ of catalyst (bed volume)·h). [Standard cubic meter=volume converted to standard conditions (20° C., 1 bar abs.)]. Reported catalyst volumes always relate to the bed volume.

The amination of the alcohol group of the reactant MIPOA is conducted in the liquid phase. Preference is given to the fixed bed process.

When working in the liquid phase, the reactants (MIPOA, ammonia) are passed, preferably simultaneously, including hydrogen, over the catalyst, which is typically situated in a fixed bed reactor preferably heated from the outside, in the liquid phase at pressures of 60 to 170 bar, preferably 70 to 145 bar, more preferably 80 to 140 bar, more preferably 90 to 135 bar, particularly preferably 100 to 130 bar, for example 110 to 125 bar, and at temperatures of 120 to 240° C., particularly 130 to 230° C., preferably 140 to 220° C., especially 150 to 210° C., more particularly 160 to 200° C., more particularly still 162 to 190° C., for example 165 to 180° C.

The temperature is selected such that there is a certain conversion of MIPOA at a given pressure. The reaction is typically operated at conversions of 70% to 100%, preferably 80% to 99.9%, likewise preferably 82% to 99.5%. The conversion is calculated as follows:

$$U = \left(1 - \frac{n}{n_0}\right) \cdot 100\%$$

where n is the residual molar amount of MIPOA after reaction is complete and $n_0$ is the original molar amount of MIPOA prior to the start of the reaction. The molar amounts can be determined by means of gas chromatography, for instance as described in the examples section of this application.

When working in the liquid phase, both a trickle mode and a liquid phase mode are possible. The liquid phase mode is preferred. The catalyst hourly space velocity is generally in the range from 0.1 to 0.7, preferably 0.15 to 0.6, particularly preferably 0.2 to 0.5, kg of MIPOA per liter of catalyst (bed volume) and per hour (MIPOA calculated as 100% by weight). The reactants may optionally be diluted with a suitable solvent, such as water, tetrahydrofuran, dioxane, N-methylpyrrolidone, or ethylene glycol dimethyl ether. The reactants are preferably not diluted with a solvent, that is to say the reaction according to the invention is effected without solvent. It is expedient to heat the reactants, preferably to the reaction temperature, even before they are supplied to the reaction vessel.

The reaction is conducted in the presence of 1.0% to 4.5% by weight of hydrogen, particularly in the presence of 1.2% to 4.5% by weight of hydrogen, more particularly in the presence of 1.5% to 4.0% by weight of hydrogen, very particularly in the presence of 2.0% to 4.0% by weight of hydrogen, more particularly still in the presence of 2.5% to 3.7% by weight of hydrogen, in each case based on the amount of MIPOA used.

The pressure in the reaction vessel, which results from the sum of the partial pressures of ammonia, of MIPOA and of the reaction products formed and also of any additionally used solvent at the indicated temperatures, is expediently increased to the desired reaction pressure (absolute pressure) by injecting hydrogen. Unless explicitly stated otherwise, all specifications of pressure given herein refer to the absolute pressure.

In addition, the excess ammonia can be circulated together with the hydrogen.

If the catalyst is arranged in the form of a fixed bed, it may be advantageous for the selectivity of the reaction to mix the shaped catalyst bodies in the reactor with inert random packings, to "dilute" them, so to speak. The proportion of the random packings in such catalyst preparations may be from 20 to 80, particularly from 30 to 60, and especially from 40 to 50 parts by volume.

The water of reaction formed in the course of the reaction (in each case one mole per mole of alcohol group converted) in general has no detrimental effect on the degree of conversion, the reaction rate, the selectivity, or the catalyst lifetime, and is therefore usefully removed from the reaction product, for example by distillation, only when said product is worked up.

The product from the reaction according to the invention may be worked up further. Typically, the reaction is effected in a reactor the output of which (after it has optionally expediently been decompressed in order to remove excess hydrogen) is separated by distillation, wherein (1) the reactor output is supplied to a first distillation column K1 in which ammonia is removed at a side draw or overhead,
(2) the bottoms output from K1 is supplied to a second distillation column K2 in which water is removed at a side draw or overhead,
(3) the bottoms output from K2 is supplied to a third distillation column K3 in which 1,2-PDA is removed at a side draw or overhead,
(4) the bottoms output from K3 is supplied to a fourth distillation column K4 in which DMDETA is removed in the bottoms, MIPOA is removed at a side draw and low boilers are removed overhead.

The ammonia, the water and 1,2-PDA are preferably each removed overhead.

The reactant MIPOA is preferably removed in gaseous form. The side draw is preferably located in the stripping section of K4.

In K4, low boilers (for example piperazines, in particular dimethylpiperazine) are usually removed overhead. Low boilers refers to those organic components which under the distillation conditions given (pressure and temperature) have a lower boiling point than 2-aminopropan-1-ol or 1-aminopropan-2-ol, depending on which of the two has the lower boiling point under the distillation conditions given. Low boilers are in particular organic components having a boiling point of <159° C. (1.013 bar).

The ammonia obtained in step (1) and/or the MIPOA obtained in step (4) can be recycled into the reactor. Preferably, both are recycled.

Ammonia removed in step (1) is recycled into the reaction particularly with a purity of 90% to 99.9% by weight, more particularly 95% to 99.9% by weight, wherein in a particular embodiment a portion of the ammonia removed, particularly 1% to 30% by weight of the ammonia removed, more particularly 2% to 20% by weight of the ammonia removed, is discharged.

The 1,2-PDA obtained in step (3) typically has a purity of 90% to 99.98% by weight, in particular 95% to 99.9% by weight.

MIPOA removed in step (4) is recycled into the reaction particularly with a purity of 90% to 99.9% by weight, more particularly 95% to 98% by weight.

DMDETA removed in step (4) usually has a purity of 90% to 99.9% by weight, in particular 94% to 97.5% by weight.

The top pressure in K1 is preferably 10 to 25 bar, particularly preferably 15 to 20 bar and very particularly preferably 17 to 19 bar. The top temperature is preferably 20 to 70° C., particularly preferably 30 to 60° C. and very particularly preferably 40 to 50° C. The bottom temperature is preferably 180 to 250° C., particularly preferably 190 to 240° C. and very particularly preferably 200 to 230° C.

The top pressure in K2 is preferably 0.3 to 2.5 bar, particularly preferably 0.5 to 2 bar and very particularly preferably 1 to 1.5 bar. The top temperature is preferably 80 to 150° C., particularly preferably 90 to 130° C. and very particularly preferably 100 to 120° C. The bottom temperature is preferably 100 to 200° C., particularly preferably 110 to 160° C. and very particularly preferably 120 to 150° C.

The top pressure in K3 is preferably 0.1 to 3 bar, particularly preferably 0.4 to 2 bar and very particularly preferably 0.5 to 1.5 bar. The top temperature is preferably 20 to 200° C., particularly preferably 50 to 190° C. and very particularly preferably 80 to 150° C. The bottom temperature is preferably 100 to 300° C., particularly preferably 120 to 250° C. and very particularly preferably 130 to 200° C.

The top pressure in K4 is preferably 0.1 to 3 bar, particularly preferably 0.3 to 1.5 bar and very particularly preferably 0.5 to 1 bar. The top temperature is preferably 80 to 200° C., particularly preferably 100 to 190° C. and very particularly preferably 120 to 170° C. The bottom temperature is preferably 100 to 300° C., particularly preferably 150 to 250° C. and very particularly preferably 190 to 220° C.

In a further distillation stage (step (5)), the DMDETA removed in the bottom of distillation column K4 can be supplied to a fifth distillation column K5 in which DMDETA having a reduced APHA color number is removed overhead. The distillation in K5 is preferably effected in the presence of an additive for improving the APHA color number, for example $NaBH_4$ or phosphonic acid.

The DMDETA thus prepared typically has an APHA color number of ≤20, particularly ≤15, very particularly ≤10, for example 2 to 8.

APHA color numbers are determined in accordance with DIN EN 1557.

Suitable distillation columns K1 to K5 include all possible column types known to those skilled in the art. Preference is given to packed columns having structured packings or random packings and also tray columns having trays such as sieve trays, bubble-cap trays or valve trays.

No such distillation process for preparing 1,2-PDA and DMDETA has been described in the prior art. The following advantages, which are surprising to those skilled in the art, result in particular. DMDETA with a high purity can be prepared with the aid of the fourth distillation column K4. DMDETA having the above-mentioned purity and formed as coproduct in the preparation of 1,2-PDA has not been described anywhere in the prior art. Further surprising advantages result with respect to the recycling of MIPOA. For instance, it has been found that there is no accumulation of by-products (for example methyl- or dimethylpiperazines). It is therefore not necessary to discharge a portion of the MIPOA which is preferably present in the abovementioned purity. This constitutes a considerable economic advantage because the MIPOA removed can thus be recycled fully into the reaction.

FIG. 1 shows a particular embodiment of the process according to the invention, in which 1,2-PDA and DMDETA are obtained by means of a 4-column interconnection.

The examples which follow serve to elucidate the invention without restricting it in any way.

EXAMPLES

The catalyst is produced in accordance with example B3 according to WO2013/072289 A1.

DESCRIPTION OF THE EXPERIMENTS

Results:

The results are given in tables 1 and 2 for various molar ratios of ammonia to MIPOA.

Example 1 (According to the Invention, Table 1, Entry 1)

A tubular reactor was filled with 47 ml of the catalyst. After activation of the catalyst under hydrogen, 18 g/h of a mixture of 1-aminopropan-2-ol and 2-aminopropan-1-ol (95:5), 42 g/h of ammonia (molar ratio 10) and 6 l (STP)/h of hydrogen (2.9% by weight based on MIPOA) were continuously passed into the reactor at 120 bar and a temperature of 165° C. After decompressing the reaction output to standard pressure, the composition was analyzed by gas chromatography. The product stream comprised 78.9% 1,2-PDA and 2.87% DMDETA and 12.2% 1-aminopropan-2-ol and 2.85% 2-aminopropan-1-ol (percentages relate to GF area %)

Example 2 (not According to the Invention, Table 1, Entry 2)

A tubular reactor was filled with 47 ml of the catalyst. After activation of the catalyst under hydrogen, 18 g/h of 1-aminopropan-2-ol and 2-aminoproan-1-ol (95:5), 42 g/h of ammonia (molar ratio 10) and 6 l (STP)/h of hydrogen were continuously passed into the reactor at 120 bar and a temperature of 175° C. After decompressing the reaction output to standard pressure, the composition was analyzed by gas chromatography. The product stream comprised 79.4% 1,2-PDA and 2.61% DMDETA and 12.0% 1-aminopropan-2-ol and 2.74% 2-aminopropan-1-ol (percentages relate to GF area %)

The remaining experiments were conducted analogously. The results are compiled in tables 1 and 2.

The GC analysis for determination of the conversion and the selectivity was effected on a 30 m RTX-5 column. The samples were injected at 50° C. After five minutes at this temperature, heating was effected to 280° C. at 5° C./minute and the oven was held at this temperature for 5 minutes.

TABLE 1

(results for MR = 10)

| Entry | MR | Pressure/bar | Temperature/ °C. | Conversion | Sel. for (1,2-PDA) | Sel. for (DMDETA) | Sel. for (1,2-PDA + DMDETA) |
| --- | --- | --- | --- | --- | --- | --- | --- |
| 1 (according to the invention) | 10 | 120 | 165 | 85% | 93% | 3% | 96% |
| 2 (not according to the invention) | 10 | 200 | 175 | 85% | 93% | 3% | 96% |
| 3 (according to the invention) | 10 | 120 | 180 | 98% | 80% | 6% | 86% |
| 4 (not according to the invention) | 10 | 200 | 195 | 98% | 77% | 4% | 81% |

MR = molar amount of ammonia based on MIPOA
Conversion: Conversion based on MIPOA
Sel. for (1,2-PDA): selectivity based on 1,2-PDA
Sel. for (DMDETA): selectivity based on DMDETA
Sel. for (1,2-PDA + DMDETA): selectivity based on 1,2-PDA and DMDETA
The temperature was set so that the desired conversion of 85% or 98% was achieved.

TABLE 2

(results for MR = 12)

| Entry | MR | Pressure/bar | Temperature/ °C. | Conversion | Sel. for (1,2-PDA) | Sel. for (DMDETA) | Sel. for (1,2-PDA + DMDETA) |
| --- | --- | --- | --- | --- | --- | --- | --- |
| 1 (according to the invention) | 12 | 120 | 165 | 87% | 93% | 3% | 96% |
| 2 (not according to the invention) | 12 | 200 | 175 | 87% | 93% | 3% | 96% |

TABLE 2-continued (results for MR = 12)

| Entry | MR | Pressure/bar | Temperature/ °C. | Conversion | Sel. for (1,2-PDA) | Sel. for (DMDETA) | Sel. for (1,2-PDA + DMDETA) |
|---|---|---|---|---|---|---|---|
| 3 (according to the invention) | 12 | 120 | 180 | 99% | 82% | 5% | 87% |
| 4 (not according to the invention) | 12 | 200 | 195 | 99% | 77% | 3% | 80% |

MR = molar amount of ammonia based on MIPOA
Conversion: Conversion based on MIPOA
Sel. for (1,2-PDA): selectivity based on 1,2-PDA
Sel. for (DMDETA): selectivity based on DMDETA
Sel. for (1,2-PDA + DMDETA): selectivity based on 1,2-PDA and DMDETA
The temperature was set so that the desired conversion of 87% or 99% was achieved.

DISCUSSION OF THE RESULTS

The results show that for conversions of 85% and 87% there is no reduction in the selectivities for 1,2-PDA and DMDETA when the pressure is reduced from 200 bar to 120 bar. At higher conversions (98% and 99%), an increase in the selectivities for 1,2-PDA and DMDETA can even be observed when the pressure is reduced from 200 bar to 120 bar. These results are surprising to those skilled in the art and cannot be derived from the prior art either alone or in combination with general technical knowledge.

The formation of 1,2-PDA and DMDETA and also the (undesired) cyclization of the latter to give dimethylpiperazine can be described by means of the following reaction scheme:

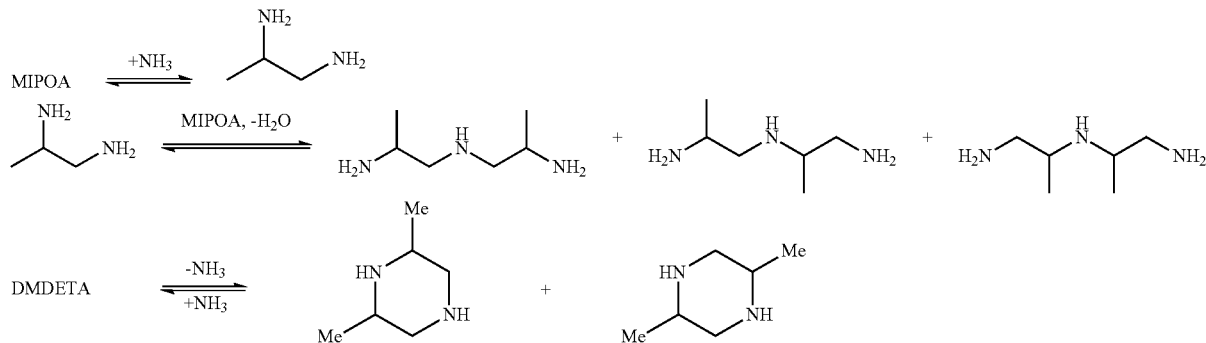

Those skilled in the art would expect better selectivity in terms of 1,2-PDA to be achieved at higher pressures (200 bar) than at lower pressures (120 bar). The conversion of 1,2-PDA is effected in the liquid phase according to the invention. The higher the pressure, the greater the amount of ammonia dissolved in the liquid phase. The more ammonia available there, the more rapidly the MIPOA can react with it. That is to say, the probability of (still) unconverted MIPOA being converted in a possible side reaction decreases. Consequently, those skilled in the art would have expected that the selectivity for 1,2-PDA would also decrease in the event of a reduction in the pressure (from 200 bar to 120 bar).

Likewise, those skilled in the art would have expected that better selectivity in terms of DMDETA would be achieved at higher pressures (200 bar) than at lower pressures (120 bar). The decrease in the selectivity for DMDETA results in particular from the fact that this cyclizes to give dimethylpiperazine with elimination of ammonia. Those skilled in the art would in fact expect the formation of dimethylpiperazine to be reduced at higher pressures in accordance with Le Chatelier's principle, since a higher pressure counteracts the elimination of ammonia. In this respect, the results presented in tables 1 and 2 show precisely the opposite to what those skilled in the art would have expected, and are therefore surprising.

Distillative Work-Up

The liquid reaction output is worked up in a distillation section.

The following examples are based on simulation results obtained with the Aspen software from Aspen Technology, Inc. The thermodynamic parameters used in the program for the individual reaction products are based on published thermodynamic data or in-house measurements. The specification and the simulation of the specified distillation columns used were effected with the customary routines included in the software.

To optimize the simulation model, the simulated results were compared with experimental results, where available, and the simulation model was aligned with the experimental results so that a good agreement between simulation and experimental data was achieved.

The following examples were computed using the optimized simulation model.

The workup was effected in four columns, as illustrated in FIG. 1.

Ammonia column (distillation column K1)

Excess ammonia is removed overhead by means of the ammonia column and recycled into the synthesis stage.

Distillation conditions:
Top pressure: 18 bar
Top temperature: 45° C.
Bottom temperature: 217° C.

The bottoms of the ammonia column still comprise water, the products of value 1,2-PDA and DMDETA and also unconverted MIPOA, and are fed to the water column (distillation column K2).

Water column (distillation column K2)

The water of reaction is removed overhead in the column.
Distillation conditions:
Top pressure: 1.25 bar
Top temperature: 104° C.
Bottom temperature: 135° C.

The bottoms (comprising MIPOA, 1,2-PDA, DMDETA and impurities) are supplied to the 1,2-PDA column (distillation column K3).

1,2-PDA column (distillation column K3)

In the 1,2-PDA column, 1,2-PDA with a purity of ≥99.8% by weight is removed overhead.
Distillation conditions:
Top pressure: 0.95 bar (950 mbar)
Top temperature: 119° C.
Bottom temperature: 158° C.

The bottoms (MIPOA, DMDETA and impurities) are supplied to the DMDETA column (distillation column K4).

DMDETA Column (Distillation Column K4)

The unconverted MIPOA is purified in the column before it is fed back to the reaction according to the invention. For this purpose, an azeotrope of MIPOA and methylpiperazine is discharged overhead.
Distillation conditions:
Top pressure: 0.76 bar (760 mbar)
Top temperature: 147° C.
Bottom temperature: 202° C.

The reactant MIPOA which has been freed from dimethylpiperazines is obtained in gaseous form with a purity of ≥97% by weight at the side draw in the stripping section of the column. DMDETA with a purity of ≥96% by weight is obtained in the bottom and is discharged.

The invention claimed is:

1. A process for the continuous preparation of 1,2-propylenediamine (1,2-PDA) and dimethyldiethylenetriamine (DMDETA) via reaction of monoisopropanolamine (MIPOA) with ammonia in the presence of hydrogen and a supported heterogeneous hydrogenation catalyst (catalyst), wherein the reaction is effected in a reactor in the liquid phase at an absolute pressure in the range from 60 to 170 bar and the reactor output is separated by distillation, wherein
   (1) the reactor output is supplied to a first distillation column K1 in which ammonia is removed at a side draw or overhead,
   (2) the bottoms output from K1 is supplied to a second distillation column K2 in which water is removed at a side draw or overhead,
   (3) the bottoms output from K2 is supplied to a third distillation column K3 in which 1,2-PDA is removed at a side draw or overhead,
   (4) the bottoms output from K3 is supplied to a fourth distillation column K4 in which DMDETA is removed in the bottoms, MIPOA is removed at a side draw and low boilers are removed overhead.

2. The process according to claim 1, wherein the ammonia obtained in step (1) and/or the MIPOA obtained in step (4) are recycled into the reaction.

3. The process according to claim 1, wherein the catalytically active composition of the catalyst, prior to the reduction thereof with hydrogen, comprises oxygen-containing compounds of aluminum and oxygen-containing compounds of copper, of nickel and/or of cobalt.

4. The process according to claim 1, wherein the catalytically active composition of the catalyst, prior to the reduction thereof with hydrogen, comprises oxygen-containing compounds of aluminum, of copper, of nickel and of cobalt and in the range from 0.2% to 5.0% by weight of oxygen-containing compounds of tin, calculated as SnO.

5. The process according to claim 1, wherein the catalytically active composition of the catalyst, prior to the reduction thereof with hydrogen, comprises in the range from 0.4% to 4.0% by weight of oxygen-containing compounds of tin, calculated as SnO.

6. The process according to claim 1, wherein the catalytically active composition of the catalyst, prior to the reduction thereof with hydrogen, comprises in the range from 5.0% to 35% by weight of oxygen-containing compounds of cobalt, calculated as CoO.

7. The process according to claim 1, wherein the catalytically active composition of the catalyst, prior to the reduction thereof with hydrogen, comprises in the range from 10% to 30% by weight of oxygen-containing compounds of cobalt, calculated as CoO.

8. The process according to claim 1, wherein the catalytically active composition of the catalyst, prior to the reduction thereof with hydrogen, comprises in the range from 15% to 80% by weight of oxygen-containing compounds of aluminum, calculated as $Al_2O_3$, 1.0% to 20% by weight of oxygen-containing compounds of copper, calculated as CuO, and 5.0% to 35% by weight of oxygen-containing compounds of nickel, calculated as NiO.

9. The process according to claim 1, wherein the catalytically active composition of the catalyst, prior to the reduction thereof with hydrogen, comprises in the range from 30% to 70% by weight of oxygen-containing compounds of aluminum, calculated as $Al_2O_3$, 2.0% to 18% by weight of oxygen-containing compounds of copper, calculated as CuO, and 10% to 30% by weight of oxygen-containing compounds of nickel, calculated as NiO.

10. The process according to claim 1, wherein the catalytically active composition of the catalyst does not comprise any rhenium and/or ruthenium.

11. The process according to claim 1, wherein the catalytically active composition of the catalyst does not comprise any iron and/or zinc.

12. The process according to claim 1, wherein the catalytically active composition of the catalyst does not comprise any oxygen-containing compounds of silicon and/or of zirconium.

13. The process according to claim 1, wherein the absolute pressure is in the range from 70 to 145 bar.

14. The process according to claim 1, wherein the reaction temperature during the reaction is 160-195° C.

15. The process according to claim 1, wherein the reaction is effected in the presence of 1.2% to 4.5% by weight of hydrogen, based on the amount of MIPOA used.

16. The process according to claim 1, wherein the ammonia is used in a 5-fold to 30-fold molar amount based on MIPOA.

* * * * *